(12) United States Patent
Kurita et al.

(10) Patent No.: US 11,717,807 B2
(45) Date of Patent: Aug. 8, 2023

(54) METHOD FOR PRODUCING CONJUGATED DIENE

(71) Applicants: NATIONAL UNIVERSITY CORPORATION CHIBA UNIVERSITY, Chiba (JP); JGC Corporation, Yokohama (JP)

(72) Inventors: Kento Kurita, Chiba (JP); Yuchao Wang, Chiba (JP); Satoshi Sato, Chiba (JP); Atsushi Okita, Yokohama (JP); Kazunori Honda, Yokohama (JP)

(73) Assignees: NATIONAL UNIVERSITY CORP. CHIBA UNIVERSITY; JGC HOLDINGS CORPORATION

( * ) Notice: Subject to any disclaimer, the term of this patent is extended or adjusted under 35 U.S.C. 154(b) by 0 days.

(21) Appl. No.: 17/845,858

(22) Filed: Jun. 21, 2022

(65) Prior Publication Data

US 2022/0323939 A1    Oct. 13, 2022

Related U.S. Application Data

(62) Division of application No. 17/260,704, filed as application No. PCT/JP2019/015183 on Apr. 5, 2019, now abandoned.

(30) Foreign Application Priority Data

Aug. 3, 2018   (JP) .............................. 2018-147062A

(51) Int. Cl.
*B01J 23/02* (2006.01)
*B01J 21/06* (2006.01)
*B01J 37/08* (2006.01)
*C07C 1/24* (2006.01)

(52) U.S. Cl.
CPC ............. *B01J 23/02* (2013.01); *B01J 21/066* (2013.01); *B01J 37/082* (2013.01); *C07C 1/24* (2013.01); *C07C 2521/06* (2013.01); *C07C 2523/02* (2013.01)

(58) Field of Classification Search
CPC ........ B01J 23/02; B01J 21/066; B01J 37/082; C07C 1/24; C07C 2521/06; C07C 2523/02
USPC ................... 585/610; 502/340, 349
See application file for complete search history.

(56) References Cited

U.S. PATENT DOCUMENTS

| | | | |
|---|---|---|---|
| 4,028,424 A | 6/1977 | Yoshida | |
| 4,593,145 A | 6/1986 | Ninagawa | |
| 4,810,680 A | 3/1989 | Bickford | |
| 2005/0124840 A1 | 6/2005 | Chen | |
| 2009/0325791 A1 | 12/2009 | Pan | |
| 2010/0056370 A1 | 3/2010 | Shigyo | |
| 2016/0184810 A1* | 6/2016 | Wright | B01J 37/009 585/329 |
| 2017/0209851 A1 | 7/2017 | Hajimoto | |
| 2017/0313633 A1 | 11/2017 | Vecchini | |
| 2021/0275994 A1 | 9/2021 | Takano | |

FOREIGN PATENT DOCUMENTS

| | | | | |
|---|---|---|---|---|
| CN | 107382645 | * | 11/2017 | ............. C07C 1/207 |
| JP | 2011063519 A | | 3/2011 | |
| JP | 2015054819 A | | 3/2015 | |
| JP | 2017001975 | * | 1/2017 | ............. B01J 23/02 |
| JP | 2017001975 A | | 1/2017 | |
| JP | 2017014133 A | | 1/2017 | |
| JP | 2017061429 A | | 3/2017 | |
| JP | 2017508717 A | | 3/2017 | |
| JP | 2017186272 A | * | 10/2017 | ............. B01J 27/18 |
| JP | 2018186272 A | | 11/2018 | |
| WO | WO-2014033129 A1 | * | 3/2014 | ............. C12N 9/88 |
| WO | WO-2015130451 A1 | * | 9/2015 | ............. B01J 23/02 |
| WO | WO-2016007196 A1 | * | 1/2016 | ............. B01J 29/06 |

OTHER PUBLICATIONS

Translation of Written Opinion for PCT/JP2019/015183. (Year: 2019).*
Yotsumoto, Rikako et al.: "Dehydration reaction of 1, 3-butanediol by zirconia supported calcium oxide", Proceedings of the Forum A of 118th Catalysis Society of Japan Meeting, Sep. 14, 2016 (Sep. 14, 2016), pp. 394.
Machine translation of Yotsumoto, Rikako et al.: "Dehydration reaction of 1, 3-butanediol by zirconia supported calcium oxide", Proceedings of the Forum A of 118th Catalysis Society of Japan Meeting, Sep. 14, 2016 (Sep. 14, 2016), pp. 394.
Machine Translation of JP2017001975A provided by Examiner in parent application.
Hailing Duan et al., "Selective dehydration of 2,3-butanediol to 3-buten-2-ol over ZrO2 modified with CaO." Applied Catalysis A: General 487, pp. 226-233. (Year: 2014).
Yoshitaka Matsumura et al., "Preparative chemistry of calcia-stabilized ZrO2 for vapor-phase dehydration of 1,4-butanediol." Molecular Catalysis 503, pp. 1-9. (Year: 2021).
Sagnika Pradhan et al., "CaO—ZrO2 nanocomposite oxide prepared by urea hydrolysis method as heterogeneous base catalyst for synthesis of chromene analogues.". Journal of Molecular Catalysis A: Chemical 425, pp. 297-309. (Year: 2016).

(Continued)

*Primary Examiner* — Patricia L. Hailey
(74) *Attorney, Agent, or Firm* — Jordan and Koda, PLLC

(57) ABSTRACT

Provided is a technique of producing isoprene from 3-methyl-1,3-butanediol or 1,3-butadiene from 1,3-butanediol by using a single catalyst. A catalyst produces a conjugated diene containing zirconium oxide and calcium oxide in order to produce isoprene by removing two water molecules from one 3-methyl-1,3-butanediol molecule or produce 1,3-butadiene by removing two water molecules from one 1,3-butanediol molecule. Furthermore, a method for producing a conjugated diene includes a step of obtaining a fluid containing a conjugated diene that is isoprene or 1,3-butadiene by bringing a fluid containing 3-methyl-1,3-butanediol or a fluid containing 1,3-butanediol into contact with the catalyst for producing a conjugated diene as a single catalyst so as to cause a dehydration reaction to proceed.

16 Claims, No Drawings

(56) References Cited

OTHER PUBLICATIONS

G. P. Causland et al., "Mechanical properties of zirconia, doped and undoped yttria-stabilized cubic zirconia from first-principles." Journal of Physics and Chemistry of Solids 122, pp. 51-71. (Year: 2018).

* cited by examiner

METHOD FOR PRODUCING CONJUGATED DIENE

BACKGROUND OF THE INVENTION

The present invention relates to a technique of producing isoprene or 1,3-butadiene.

Isoprene or 1,3-butadiene (hereinafter, these are also collectively referred to as a "conjugated diene") that is used as a raw material for synthetic rubber, or the like is mainly produced by naphtha cracking in which isoprene or 1,3-butadiene is produced as a co-product of ethylene by thermal decomposition of naphtha. Furthermore, regarding 1,3-butadiene, a single production process such as an oxydehydrogenation process of butene or a dimerization process of ethanol or acetaldehyde is also known.

Other than the above, the development of a process of producing 1,3-butadiene from an alcohol, which can be produced from a biomass-derived raw material by a fermentation method or the like without being limited to a petrochemical raw material has been conducted as a single production process with a small environmental load in various ways.

Of them, particularly, the development of a catalyst capable of causing a reaction of producing a conjugated diene by using a single catalyst to proceed and a simple process suitable for this catalyst becomes important.

For example, Patent Documents 1 to 4 describe a technique of using a catalyst obtained by combination of zirconium oxide and calcium as a catalyst producing an unsaturated alcohol having one double bond from various C4 diol-type compounds.

However, these patent documents do not disclose a technique of producing a conjugated diene from diol-type compounds with a simple process.

Furthermore, Patent Document 5 describes a technique in which a dehydration reaction of a 1,3-diol type raw material is caused to proceed by using, as a catalyst, zirconia containing, as a dopant, an element selected from an alkaline-earth element and a rare-earth element to obtain an unsaturated alcohol, and then a dehydration reaction of the unsaturated alcohol is caused to proceed by using a dehydration catalyst such as a silica alumina catalyst to obtain a diene compound such as 1,3-butadiene.

However, in the method described in Patent Document 5, plural kinds of catalysts are necessary, and a process of obtaining a diene compound is complicated.

CITATION LIST

Patent Document

Patent Document 1: JP-A-2015-54819
Patent Document 2: JP-A-2017-1975
Patent Document 3: JP-A-2017-14133
Patent Document 4: JP-A-2017-61429
Patent Document 5: JP-A-2017-186272

SUMMARY OF THE INVENTION

The invention has been made under such a background and provides a technique of producing isoprene from 3-methyl-1,3-butanediol or 1,3-butadiene from 1,3-butanediol by using a single catalyst.

The invention is a catalyst for producing a conjugated diene, causing a reaction of removing two water molecules from one 3-methyl-1,3-butanediol molecule to produce isoprene to proceed or a catalyst for producing a conjugated diene, causing a reaction of removing two water molecules from one 1,3-butanediol molecule to produce 1,3-butadiene to proceed, the catalyst characterized by containing zirconium oxide and calcium oxide.

The catalyst for producing a conjugated diene is used under a condition that a mass flow rate (WHSV: Weight Hourly Space Velocity) of the 3-methyl-1,3-butanediol or the 1,3-butanediol per unit time with respect to a weight of the catalyst for producing a conjugated diene is 1.5 $h^{-1}$ or less.

At this time, a content ratio may be adjusted so that a content of calcium atom of the calcium oxide with respect to 1 mol of zirconium atom of the zirconium oxide is within a range of 0.01 mol or more and 0.3 mol or less.

The calcium oxide may be supported on the zirconium oxide.

Regarding the zirconium oxide, a case where the zirconium oxide has a tetragonal form or a cubic form can be exemplified. At this time, the zirconium oxide may be configured by yttria-stabilized zirconia (YSZ).

Furthermore, a method for producing the catalyst for producing a conjugated diene is characterized by including a step of calcining the zirconium oxide or a precursor containing zirconium at a temperature within a range of 700° C. or higher and 1200° C. or lower.

Further, a method for producing a conjugated diene of the invention is characterized by including a step of obtaining a fluid containing a conjugated diene that is isoprene by bringing a fluid containing 3-methyl-1,3-butanediol into contact with the catalyst for producing a conjugated diene to remove two water molecules from one 3-methyl-1,3-butanediol molecule or including a step of obtaining a fluid containing a conjugated diene that is 1,3-butadiene by bringing a fluid containing 1,3-butanediol into contact with the catalyst for producing a conjugated diene to remove two water molecules from one 1,3-butanediol molecule.

Herein, it is suitable that, in the step of obtaining a fluid containing a conjugated diene, a mass flow rate (WHSV) of the 3-methyl-1,3-butanediol or the 1,3-butanediol per unit time with respect to a weight of the catalyst for producing a conjugated diene is 1.5 $h^{-1}$ or less. Further, this step is preferably performed at a reaction temperature within a range of 250° C. or higher and 400° C. or lower. Other than the above, the method may include a step of calcining the catalyst for producing a conjugated diene at a temperature within a range of 700° C. or higher and 1200° C. or lower before performing the step of obtaining a fluid containing a conjugated diene.

This catalyst for producing a conjugated diene can cause the dehydration reaction of removing two water molecules from one 3-methyl-1,3-butanediol molecule to produce isoprene or removing two water molecules from one 1,3-butanediol molecule to produce 1,3-butadiene to proceed, and thus a conjugated diene can be efficiently produced with a simple process from these raw materials.

DETAILED DESCRIPTION OF PREFERRED EMBODIMENTS OF THE INVENTION

<Catalyst for Producing Conjugated Diene and Production Method Therefor>

A catalyst for producing a conjugated diene of this example contains zirconium oxide and calcium oxide and causes a dehydration reaction of the following Formula (1) in which two water molecules are removed from one 3-methyl-1,3-butanediol molecule (hereinafter, also referred to as "3M1,3BDO") to produce isoprene to proceed.

[Chemical Formula 1]

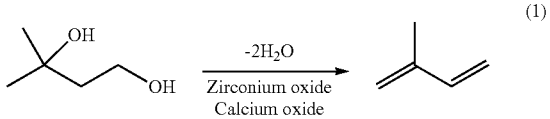

(1)

Alternatively, the above-described catalyst for producing a conjugated diene causes a dehydration reaction of the following Formula (2) in which two water molecules are removed from one 1,3-butanediol molecule (hereinafter, also referred to as "1,3BDO") to produce 1,3-butadiene to proceed.

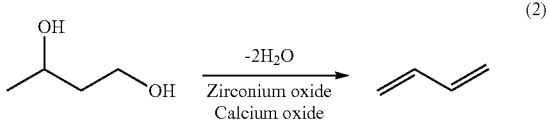

(2)

The catalyst for producing a conjugated diene of this example enables a process of producing a conjugated diene by causing a dehydration reaction from 3M1,3BDO or 1,3BDO to proceed by using a single catalyst, which is conventionally considered to be difficult, to be realized.

The configuration of the zirconium oxide contained in the catalyst for producing a conjugated diene and the preparation method thereof are not particularly limited. Commercially available zirconium oxide may be used, and zirconium oxide obtained by calcining a precursor containing zirconium such as zirconium chloride in an oxygen atmosphere, or the like may be used. Furthermore, as the zirconium oxide, tetragonal zirconium oxide and cubic zirconium oxide may be used.

The tetragonal or cubic zirconium oxide may be yttria-stabilized zirconia (YSZ) that is zirconia stabilized by yttria.

The configuration of the calcium oxide contained in the catalyst for producing a conjugated diene and the preparation method thereof are also not particularly limited. Commercially available calcium oxide may be used, and calcium oxide obtained by calcining a precursor containing calcium such as calcium nitrate or calcium hydroxide in an oxygen atmosphere, or the like may be used. Furthermore, calcia-stabilized zirconia (CSZ) that is zirconia stabilized by calcia may be used.

The zirconium oxide contained in the catalyst for producing a conjugated diene causes the dehydration reaction of 3M1,3BDO or 1,3BDO to proceed. On the other hand, the calcium oxide acts as a base and suppresses the acidity of the zirconium oxide. As a result, the proceeding of a decomposition reaction of 3M1,3BDO or 1,3BDO is suppressed, and accordingly, the selectivity of a target material is enhanced. Furthermore, it is considered that the acid site of the zirconium oxide and the base site of the calcium oxide concertedly act, and thereby the reaction activity is improved as compared to the case of using the zirconium oxide alone.

From the viewpoint of effectively bringing the zirconium oxide and the calcium oxide into contact with the raw material fluid containing 3M1,3BDO or 1,3BDO, the zirconium oxide and the calcium oxide may be contained, for example, in a state of fine particles of nanometer order to micrometer order, in the catalyst for producing a conjugated diene.

Furthermore, like the already-described calcia-stabilized zirconia or the like, the zirconium oxide and the calcium oxide may be configured as a composite oxide containing a calcium atom in the skeletal structure of the zirconium oxide.

The catalyst for producing a conjugated diene may be configured by supporting fine particulate zirconium oxide or calcium oxide, or a composite oxide thereof on a carrier. In order to suppress the production of a by-product, it is preferable to use a carrier having no reaction activity with respect to 3M1,3BDO or 1,3BDO or a carrier having a small specific surface area and substantially having no effect on the reaction.

As such a carrier, a carrier containing at least one carrier raw material selected from the carrier raw material group consisting of silica, α-alumina, carbon, and silicon carbide can be exemplified.

The catalyst for producing a conjugated diene may be configured by dispersedly supporting zirconium oxide, calcium oxide, or a composite oxide thereof on a surface of a powdery carrier having a diameter larger than the above-described fine particle. Furthermore, the catalyst for producing a conjugated diene may be configured, for example, by dispersedly supporting zirconium oxide, calcium oxide, or a composite oxide thereof on a surface of a carrier molded into a granular shape or a ring shape.

The method of dispersedly supporting zirconium oxide, calcium oxide, or a composite oxide thereof on a carrier is not particularly limited. For example, known supporting methods such as an impregnation method, a precipitation method, and a kneading method can be used.

Upon performing the aforementioned various supporting methods, a precursor of zirconium oxide, calcium oxide, or a composite oxide thereof may be supported on a surface of a carrier by using these methods, and then calcination may be performed to convert each precursor dispersedly supported on the surface of the carrier into zirconium oxide, calcium oxide, or a composite oxide thereof.

Furthermore, in a case where the catalyst for producing a conjugated diene obtained after zirconium oxide, calcium oxide, or a composite oxide thereof is supported has a powdery shape, the catalyst may be molded into a granular shape, a ring shape, or the like, depending on the usage aspect in the production process of a conjugated diene.

Further, in a case where the catalyst for producing a conjugated diene is configured by zirconium oxide and calcium oxide, the catalyst for producing a conjugated diene may be configured by dispersedly supporting calcium oxide on a surface of powdery zirconium oxide having a diameter larger than the fine particle of calcium oxide. Furthermore, the catalyst for producing a conjugated diene may be configured, for example, by dispersedly supporting calcium oxide on a surface of zirconium oxide molded into a granular shape or a ring shape.

The method of dispersedly supporting calcium oxide on zirconium oxide is not particularly limited. For example, known supporting methods such as an impregnation method, a precipitation method, and a kneading method can be used.

Upon supporting the calcium oxide on the zirconium oxide described above, a precursor of the calcium oxide may be supported on a surface of a precursor of the zirconium oxide by using these methods, and then calcination may be performed to convert the respective precursors into the zirconium oxide and the calcium oxide. As a result, zirconium oxide on a surface of which calcium oxide is dispersedly supported can be obtained.

Furthermore, in a case where the catalyst for producing a conjugated diene that is zirconium oxide on which calcium oxide is supported has a powdery shape, the catalyst may be molded into a granular shape, a ring shape, or the like, depending on the usage aspect in the production process of a conjugated diene.

Herein, the zirconium oxide contained in the catalyst for producing a conjugated diene is, for example, preferably zirconium oxide calcined at a temperature within a range of 700° C. or higher and 1200° C. or lower, preferably at a temperature within a range of 800° C. or higher and 1000° C. or lower. By performing calcination, zirconium oxide having a specific crystal face (for example, a tetragonal crystal face) is obtained, and thus a surface effective to this reaction can be formed. At this time, there is a concern that the catalyst for producing a conjugated diene calcined at 700° C. or lower does not sufficiently obtain a desired crystal face and the conversion rate is decreased. On the other hand, when the catalyst is calcined at a temperature of 1200° C. or higher, a surface area of the catalyst for producing a conjugated diene is decreased, and thereby the conversion rate is decreased in some cases.

Commercially available zirconium oxide, zirconium oxide subjected to a low calcination temperature when zirconium oxide is formed from a precursor, or the like is calcined at the above-described temperature range, and thereby a higher dehydration reaction activity can be exhibited. Furthermore, the calcination temperature when calcination of obtaining zirconium oxide from a precursor is performed may be set to a temperature within a range of 700° C. or higher and 1200° C. or lower, and then, the formation of zirconium oxide may be performed along with a treatment of obtaining a predetermined crystal face.

The calcination atmosphere may be, for example, an air atmosphere and an inert gas atmosphere such as nitrogen gas.

Furthermore, the calcination of the zirconium oxide may be performed at any time as long as it is performed before the reaction, and the calcination thereof may be performed at the time of producing a catalyst or at the timing after the catalyst is filled in a reactor for a production process of a conjugated diene.

It is preferable that the aforementioned catalyst for producing a conjugated diene is used under the condition that the mass flow rate (WHSV: Weight Hourly Space Velocity) of 3M1,3BDO or 1,3BDO per unit time with respect to the weight of the catalyst for producing a conjugated diene filled in the above-described reactor is 1.5 $h^{-1}$ or less.

Regarding the content ratio of the zirconium oxide and the calcium oxide in the catalyst for producing a conjugated diene of this example, the content of calcium atom of the calcium oxide with respect to 1 mol of zirconium atom of the zirconium oxide is preferably within a range of 0.01 mol or more and 0.3 mol or less. More preferably, the content of calcium atom may be within a range of 0.05 mol or more and 0.3 mol or less.

In a case where the content of calcium atom is less than 0.01 mol, there is a concern that the action of suppressing the progress of the decomposition reaction of 3M1,3BDO or 1,3BDO or the concerted action between the acid site of the zirconium oxide and the base site of the calcium oxide is not sufficiently obtained. Furthermore, in a case where the content of calcium atom exceeds 0.3 mol, there is a concern that the dehydration reaction of 3M1,3BDO or 1,3BDO at the zirconium oxide side is inhibited.

<Method for Producing Conjugated Diene>

A method for producing a conjugated diene, which includes producing isoprene from 3M1,3BDO or producing 1,3-butadiene from 1,3BDO, by using the catalyst for producing a conjugated diene described above will be described.

For example, a powdery catalyst for producing a conjugated diene can be used in a reactor of a fluidized bed type, a suspended bed type, a moving bed type, or the like, and a catalyst for producing a conjugated diene molded into a granular shape, a ring shape, or the like can be used in a fixed bed type reactor.

Herein, in a case where a reactor accommodating a catalyst for producing a conjugated diene has sufficient heat resistance, or the like, a step of calcining the catalyst for producing a conjugated diene at the aforementioned temperature within the range of 700° C. or higher and 1200° C. or lower, preferably a temperature within a range of 800° C. or higher and 1000° C. or lower may be performed as a pretreatment before the start of production of a conjugated diene.

Further, with respect to a reactor in which a catalyst for producing a conjugated diene having a shape corresponding to a reaction process is accommodated, a fluid of 3M1,3BDO or a fluid of 1,3BDO is heated to a predetermined temperature and supplied. As a result, the raw material fluid is brought into contact with the zirconium oxide and the calcium oxide contained in the catalyst for producing a conjugated diene in the reactor to cause the dehydration reaction from the 3M1,3BDO or 1,3BDO to proceed. Therefore, in the reaction process of this example, isoprene can be produced from the fluid of 3M1,3BDO or 1,3-butadiene can be produced from the fluid of 1,3BDO.

Herein, as 3M1,3BDO contained in the raw material fluid, a material obtained from a process of reacting 4,4-dimethyl dioxane with methanol or a process of hydrating 3-methyl-3-buten-1-ol can be used.

Furthermore, as 1,3BDO contained in the raw material fluid, a material produced by using sugar as a raw material and by a fermentation method, for example, using a smart cell can be used. Alternatively, as 1,3BDO contained in the raw material fluid is not limited to a material derived from biomass, and may be, for example, a material produced by an industrial process of reacting acetylene with formaldehyde, for example.

As for raw material fluid, the temperature in the reactor may be maintained, for example, at a temperature within a range of 250° C. or higher and 400° C. or lower, preferably 325° C. or higher and 400° C. or lower, and more preferably 340° C. or higher and 380° C. or lower. When the reaction temperature is set to 340° C. or higher, a relatively high conversion rate and a relatively high conjugated diene yield are obtained.

Furthermore, a ratio of the mass flow rate of 3M1,3BDO or 1,3BDO contained in the raw material fluid (WHSV=F/W, W: catalyst weight, F: mass flow rate of 3M1,3BDO or 1,3BDO) with respect to the weight of the catalyst accommodated in the reactor is preferably 1.5 $h^{-1}$ or less. By bringing the catalyst for producing a conjugated diene into contact with 3M1,3BDO or 1,3BDO under the condition that the WHSV is 1.5 $h^{-1}$ or less, the dehydration reaction can be caused to sufficiently proceed, and by setting the WHSV to 1.0 $h^{-1}$ or less, the dehydration reaction can be caused to further proceed.

Furthermore, in order to improve the conversion rate of 3M1,3BDO or 1,3BDO, recycle may be performed in which a part of the fluid flowing out from the reactor is extracted to be converged with the raw material fluid, and supplied to the reactor again.

The fluid flowing out from the reactor is separated from impurities by distillation or the like and then shipped out as a product conjugated diene.

According to the catalyst for producing a conjugated diene of the present embodiment and the method for producing a conjugated diene using this catalyst, the following effects are achieved. The catalyst for producing a conjugated diene can cause the dehydration reaction of removing two water molecules from one 3M1,3BDO molecule to produce isoprene or removing two water molecules from one 1,3BDO molecule to produce 1,3-butadiene to proceed, and thus a conjugated diene can be efficiently produced with a simple process from these raw materials.

In particular, the catalyst for producing a conjugated diene of this example is used under the condition that the mass flow rate (WHSV: Weight Hourly Space Velocity) of 3M1, 3BDO or 1,3BDO per unit time with respect to the weight of the catalyst for producing a conjugated diene is 1.5 $h^{-1}$ or less, and thereby a high conversion rate and a high selectivity of the conjugated diene are obtained. As a result, a basic raw material unit indicating the ratio of the weight of the conjugated diene produced from the raw material per unit weight is satisfactory.

Further, with production of a conjugated diene from 3M1,3BDO or 1,3BDO by using a single catalyst being possible, it is possible to configure a simple conjugated diene production apparatus with a simple configuration of a reactor and less ancillary facilities.

EXAMPLES

Hereinafter, specific examples of the aforementioned embodiment will be described by means of Examples; however, the invention is not limited by these Examples.

[Reaction Apparatus]

A fixed-bed normal-pressure gas-phase flow reaction apparatus was used in all of dehydration reactions shown in Examples and Comparative Examples below. A reaction tube having an inner diameter of 18 mm and a total length of 300 mm was used as a reaction tube (Pyrex (registered trademark) made of glass). An introduction port for a diluent gas and a carburetor for vaporizing a raw material are connected in series to the upper part of the reaction tube, and a cooler and a gas-liquid separator are installed at the lower part thereof. Each of the gas and the liquid produced by the reaction was separately recovered and measured by a gas chromatography apparatus (manufactured by SHIMADZU CORPORATION, GC-8A) connected with a capillary column (TC-WAX, 30 m, 0.53 mmϕ), the yield of the target material and the residual amount of the raw material were obtained after the calibration curve correction, and the conversion rate and the selectivity were obtained therefrom.

The following calculation equations were used in the calculation of the conversion rate and the selectivity.

Conversion rate=Diol consumption amount (mol)/ Diol introduction amount (mol)×100(%)     [Mathematical Formula 1]

Focus component selectivity=Focus component production amount (mol)/Diol consumption amount (mol)×100(%)     [Mathematical Formula 2]

Comparative Example 1

0.5 g of tetragonal stabilized zirconia containing 5.6 mol % of yttrium (DAIICHI KIGENSO KAGAKU KOGYO CO., LTD., YSZ, specific surface area: 79.3 $m^2/g$) (calcination temperature: 800° C.) was filled as a catalyst for producing a conjugated diene in the reaction tube of the above-described normal-pressure gas-phase flow reaction apparatus, and 3M1,3BDO (Wako Pure Chemical Industries, Ltd.) as a raw material fluid was supplied at a rate of 1.7 g/h (WHSV: 3.4 $h^{-1}$) while supplying nitrogen gas as a diluent gas at a rate of 30 mL/min. The dehydration reaction was performed at 325° C. The reaction was performed for 5 hours in total, sampling was performed every hour, and the reaction result was obtained from an average value thereof. The conversion rate of 3M1,3BDO at this time and the selectivities of isoprene as a target conjugated diene, isobutene as a decomposition by-product, and an unsaturated alcohol as an intermediate of isoprene are shown in Table 1.

Comparative Example 2

The dehydration reaction was performed under the same condition as in Comparative Example 1 described above, except that the catalyst amount was set to 5.0 g (WHSV: 0.34 $h^{-1}$) and the reaction temperature was set to 340° C. The results are shown in Table 1.

Comparative Example 3

The dehydration reaction was performed under the same condition as in Comparative Example 1 by using 0.5 g of monoclinic zirconium oxide (m-$ZrO_2$) (DAIICHI KIGENSO KAGAKU KOGYO CO., LTD., HP, pellet product pulverization, specific surface area: 100 $m^2/g$) (calcination temperature: 800° C., WHSV: 3.4 $h^{-1}$) as a catalyst. The results are shown in Table 1.

Comparative Example 4

The dehydration reaction was performed under the same condition as in Comparative Example 1 by using 0.5 g of cerium oxide (DAIICHI KIGENSOKAGAKUKOGYO CO., LTD., HS) (calcination temperature: 800° C., WHSV: 3.4 $h^{-1}$) as a catalyst. The results are shown in Table 1.

Comparative Example 5

The catalyst amount was set to 4.0 g (WHSV: 0.43 $h^{-1}$) and the dehydration reaction was performed under the same condition as in Comparative Example 4 described above at a reaction temperature of 350° C. The results are shown in Table 1.

Example 1

An aqueous solution prepared by adding distilled water in 718.1 mg of calcium nitrate tetrahydrate (Wako Pure Chemical Industries, Ltd., purity: 98.5% or more) was added in a small amount at intervals of 10 minutes to 4.98 g of tetragonal stabilized zirconia containing 5.6 mol % of yttrium (DAIICHI KIGENSO KAGAKU KOGYO CO., LTD., YSZ, specific surface area: 79.3 $m^2/g$), and then dried at 110° C. overnight. Thereafter, the obtained product was calcined at 800° C. for 3 hours in an air atmosphere, and thereby a catalyst for producing a conjugated diene in which calcium oxide is supported on zirconium oxide was prepared. The amount of the calcium oxide supported in Example 1 was 7 mol %. The following calculation equation was used in the calculation of the amount of the calcium oxide supported. The dehydration reaction was performed by using this catalyst under the same condition as in Comparative Example 1 described above, and the catalytic activity thereof (the conversion rate of 3M1,3BDO) was checked. The results are shown in Table 2. Incidentally, in Tables 2, 3, 5, and 7 shown below, the content of calcium atom of the calcium oxide with respect to 1 mol of zirconium atom of the zirconium oxide is described as "Calcium content". In this example, the content of calcium atom of the calcium oxide with respect to 1 mol of zirconium atom of the zirconium oxide corresponds to 0.08 mol.

Supported amount (mol %)=Calcium oxide (mol)/
(Zirconium oxide (mol)+Calcium oxide (mol))×
100                                              [Mathematical Formula 3]

Examples 2 to 5

A catalyst for producing a conjugated diene was prepared under the same condition as in Example 1 described above, except that the calcination temperature was changed, and the dehydration reaction was performed. The results are shown in Table 2. The respective calcination temperatures are as follows.

[Example 2] 600° C.
[Example 3] 700° C.
[Example 4] 900° C.
[Example 5] 1000° C.

Examples 6 to 10

The dehydration reaction was performed by using a catalyst for producing a conjugated diene which was prepared under the same condition as in Example 1 described above, except that the amount of the calcium nitrate tetrahydrate was changed so that the amount of the calcium oxide supported was set to 15 mol % (calcium content: 0.18) and the reaction temperature was changed. The results obtained by checking the catalytic activity of these catalysts (the conversion rate of 3M1,3BDO) are shown in Table 3. The respective reaction temperatures are as follows.

[Example 6] 275° C.
[Example 7] 300° C.
[Example 8] 325° C.
[Example 9] 350° C.
[Example 10] 375° C.

Examples 11 to 15

The dehydration reaction was performed under the same condition as in Example 9, except that the amount of the calcium oxide supported was set to be the same amount as in Example 9, a catalyst for producing a conjugated diene prepared under the same condition as in Example 1 described above was used, and the catalyst amount was changed so as to change the WHSV. The reaction catalytic activity (the conversion rate of 3M1,3BDO) and the selectivities of isoprene, isobutene, and an unsaturated alcohol are shown in Table 4 (hereinafter, the same applies in Tables 5 to 7). The respective catalyst amounts are as follows. The words in the parentheses indicate the value of the WHSV.

[Example 11] 1.0 g (1.7 h$^{-1}$)
[Example 12] 1.5 g (1.1 h$^{-1}$)
[Example 13] 2.0 g (0.85 h$^{-1}$)
[Example 14] 3.0 g (0.57 h$^{-1}$)
[Example 15] 4.0 g (0.43 h$^{-1}$)

Example 16

The dehydration reaction was performed under the same condition as in Example 11 described above, except that the catalyst amount was set to 4.0 g (WHSV: 0.43 h$^{-1}$) and the reaction temperature was set to 340° C. The results are shown in Table 4.

Example 17

The dehydration reaction was performed under the same condition as in Example 16 described above, except that the catalyst amount was set to 5.0 g (WHSV: 0.34 h$^{-1}$). The results are shown in Table 4.

Example 18

The dehydration reaction was performed under the same condition as in Example 11 described above, except that the catalyst amount was set to 3.0 g (WHSV: 0.57 h$^{-1}$) and the reaction temperature was set to 360° C. The results are shown in Table 4.

Example 19

A catalyst for producing a conjugated diene, which was prepared under the same condition as in Example 1 described above, except that the amount of the calcium nitrate tetrahydrate was changed so that the amount of the calcium oxide supported was set to 5 mol % (calcium content: 0.05), was used. The dehydration reaction was performed under the same condition as in Example 11 described above, except that the catalyst amount was set to 5.0 g (WHSV: 0.34 h$^{-1}$) and the reaction temperature was set to 340° C. The results are shown in Table 5.

Example 20

A catalyst for producing a conjugated diene, which was prepared under the same condition as in Example 1 described above, except that the amount of the calcium nitrate tetrahydrate was changed so that the amount of the calcium oxide supported was set to 10 mol % (calcium content: 0.11), was used. The dehydration reaction was performed under the same condition as in Example 11 described above, except that the catalyst amount was set to 4.0 g (WHSV: 0.43 h$^{-1}$). The results are shown in Table 5.

Example 21

A catalyst for producing a conjugated diene, which was prepared under the same condition as in Example 1 described above, except that the amount of the calcium nitrate tetrahydrate was changed so that the amount of the calcium oxide supported was set to 20 mol % (calcium content: 0.25), was used. The dehydration reaction was performed under the same condition as in Example 11 described above, except that the catalyst amount was set to 4.0 g (WHSV: 0.43 h$^{-1}$). The results are shown in Table 5.

Examples 22 and 23

A catalyst for producing a conjugated diene, which was prepared under the same condition as in Example 1 described above, except that the calcination temperature was changed, was used. The dehydration reaction was performed under the same condition as in Example 11 described above, except that the catalyst amount was set to 4.0 g (WHSV: 0.43 h$^{-1}$). The results are shown in Table 6. The respective calcination temperatures are as follows.

[Example 22] 700° C.
[Example 23] 900° C.

Example 24

The dehydration reaction was performed under the same condition as in Example 17 described above, except that the raw material fluid was changed to 1,3-butanediol. The results are shown in Table 7. In Table 7, "MEK+MVK" indicates a selectivity of methyl ethyl ketone and methyl vinyl ketone. The experiment conditions of Example 24 satisfy requisites of a WHSV of 1.5 h$^{-1}$ or less and a calcination temperature within a range of 700° C. or higher and 1200° C. or lower. Furthermore, a requisite of a reaction temperature of 250° C. or higher and 400° C. or lower is satisfied.

Example 25

The dehydration reaction was performed under the same condition as in Example 24 described above, except that the reaction temperature was set to 360° C. The results are shown in Table 7. The experiment conditions of Example 25 satisfy requisites of a WHSV of 1.5 h$^{-1}$ or less and a calcination temperature within a range of 700° C. or higher and 1200° C. or lower. Furthermore, a requisite of a reaction temperature of 250° C. or higher and 400° C. or lower is satisfied.

Example 26

The dehydration reaction was performed under the same condition as in Example 24 described above, except that the reaction temperature was set to 380° C. The results are shown in Table 7. The experiment conditions of Example 26 satisfy requisites of a WHSV of 1.5 h$^{-1}$ or less and a calcination temperature within a range of 700° C. or higher and 1200° C. or lower. Furthermore, a requisite of a reaction temperature of 250° C. or higher and 400° C. or lower is satisfied.

Comparative Example 6

The dehydration reaction was performed under the same condition as in Example 25 by using 0.5 g (WHSV: 3.4 h$^{-1}$) of cerium oxide of which a calcination temperature is 800° C. (DAIICHI KIGENSO KAGAKU KOGYO CO., LTD., HS). The results are shown in Table 7.

Comparative Example 7

The dehydration reaction was performed under the same condition as in Comparative Example 6 described above, except that the catalyst amount was set to 5.0 g (WHSV: 0.34 h$^{-1}$). The results are shown in Table 7.

TABLE 1

|  | Catalyst | Calcination temperature [° C.] | Catalyst amount [g] | WHSV [h$^{-1}$] | Reaction temperature [° C.] | 3M1,3BDO conversion rate [%] | Selectivity Isoprene [%] | Selectivity Isobutene [%] | Unsaturated alcohol [%] |
|---|---|---|---|---|---|---|---|---|---|
| Comparative Example 1 | YSZ | 800 | 0.5 | 3.4 | 325 | 63.5 | 0.3 | 2.6 | 90.1 |
| Comparative Example 2 | YSZ | 800 | 5.0 | 0.34 | 340 | 99.9 | 33.6 | 50.7 | 0 |
| Comparative Example 3 | m-ZrO$_2$ | 800 | 0.5 | 3.4 | 325 | 40.8 | 0 | 9.4 | 80.5 |
| Comparative Example 4 | CeO$_2$ | 800 | 0.5 | 3.4 | 325 | 80.3 | 1.3 | 2.9 | 88.9 |
| Comparative Example 5 | CeO$_2$ | 800 | 4.0 | 0.43 | 350 | 100 | 50.6 | 3.4 | 8.9 |

TABLE 2

|  | Catalyst | Calcium content [mol-Ca/mol-Zr] | Calcination temperature [° C.] | Catalyst amount [g] | WHSV [h$^{-1}$] | Reaction temperature [° C.] | 3M1,3BDO conversion rate [%] |
|---|---|---|---|---|---|---|---|
| Example 2 | 7 mol % CaO/YSZ | 0.08 | 600 | 0.5 | 3.4 | 325 | 24.8 |
| Example 3 | 7 mol % CaO/YSZ | 0.08 | 700 | 0.5 | 3.4 | 325 | 66.5 |
| Example 1 | 7 mol % CaO/YSZ | 0.08 | 800 | 0.5 | 3.4 | 325 | 74.6 |
| Example 4 | 7 mol % CaO/YSZ | 0.08 | 900 | 0.5 | 3.4 | 325 | 75.9 |
| Example 5 | 7 mol % CaO/YSZ | 0.08 | 1000 | 0.5 | 3.4 | 325 | 43.9 |

TABLE 3

|  | Catalyst | Calcium content [mol-Ca/mol-Zr] | Calcination temperature [° C.] | Catalyst amount [g] | WHSV [h$^{-1}$] | Reaction temperature [° C.] | 3M1,3BDO conversion rate [%] |
|---|---|---|---|---|---|---|---|
| Example 6 | 15 mol % CaO/YSZ | 0.18 | 800 | 0.5 | 3.4 | 275 | 7.5 |
| Example 7 | 15 mol % CaO/YSZ | 0.18 | 800 | 0.5 | 3.4 | 300 | 32.1 |

TABLE 3-continued

| | Catalyst | Calcium content [mol-Ca/mol-Zr] | Calcination temperature [° C.] | Catalyst amount [g] | WHSV [h$^{-1}$] | Reaction temperature [° C.] | 3M1,3BDO conversion rate [%] |
|---|---|---|---|---|---|---|---|
| Example 8 | 15 mol % CaO/YSZ | 0.18 | 800 | 0.5 | 3.4 | 325 | 80.5 |
| Example 9 | 15 mol % CaO/YSZ | 0.18 | 800 | 0.5 | 3.4 | 350 | 89.9 |
| Example 10 | 15 mol % CaO/YSZ | 0.18 | 800 | 0.5 | 3.4 | 375 | 99.5 |

TABLE 4

| | Catalyst | Catalyst amount [g] | WHSV [h$^{-1}$] | Reaction temperature [° C.] | 3M1,3BDO conversion rate [%] | Selectivity Isoprene [%] | Isobutene [%] | Unsaturated alcohol [%] |
|---|---|---|---|---|---|---|---|---|
| Example 9 | 15 mol % CaO/YSZ | 0.5 | 3.4 | 350 | 89.9 | 12.3 | 0 | 85.2 |
| Example 11 | 15 mol % CaO/YSZ | 1.0 | 1.7 | 350 | 99.8 | 29.3 | 0 | 68.2 |
| Example 12 | 15 mol % CaO/YSZ | 1.5 | 1.1 | 350 | 100 | 57.1 | 0 | 40.2 |
| Example 13 | 15 mol % CaO/YSZ | 2.0 | 0.85 | 350 | 100 | 65.6 | 1.5 | 30.1 |
| Example 14 | 15 mol % CaO/YSZ | 3.0 | 0.57 | 350 | 100 | 81.2 | 2.7 | 11.8 |
| Example 15 | 15 mol % CaO/YSZ | 4.0 | 0.43 | 350 | 100 | 92.9 | 1.5 | 0.9 |
| Example 16 | 15 mol % CaO/YSZ | 4.0 | 0.43 | 340 | 100 | 89.3 | 3.0 | 3.2 |
| Example 17 | 15 mol % CaO/YSZ | 5.0 | 0.34 | 340 | 99.8 | 91.4 | 4.6 | 0 |
| Example 18 | 15 mol % CaO/YSZ | 3.0 | 0.57 | 360 | 99.9 | 80.7 | 8.9 | 2.7 |

TABLE 5

| | Catalyst | Calcium content [mol-Ca/mol-Zr] | Catalyst amount [g] | WHSV [h$^{-1}$] | Reaction temperature [° C.] | 3M1,3BDO conversion rate [%] | Selectivity Isoprene [%] | Isobutene [%] | Unsaturated alcohol [%] |
|---|---|---|---|---|---|---|---|---|---|
| Comparative Example 2 | YSZ | — | 5.0 | 0.34 | 340 | 99.9 | 33.6 | 50.7 | 0 |
| Example 19 | 5 mol % CaO/YSZ | 0.05 | 5.0 | 0.34 | 340 | 100 | 77.0 | 11.1 | 0.2 |
| Example 20 | 10 mol % CaO/YSZ | 0.11 | 4.0 | 0.43 | 350 | 100 | 91.3 | 3.7 | 0 |
| Example 15 | 15 mol % CaO/YSZ | 0.18 | 4.0 | 0.43 | 350 | 100 | 92.9 | 1.5 | 0.9 |
| Example 21 | 20 mol % CaO/YSZ | 0.25 | 4.0 | 0.43 | 350 | 100 | 88.4 | 2.0 | 3.3 |

TABLE 6

| | Catalyst | Calcination temperature [° C.] | Catalyst amount [g] | WHSV [h$^{-1}$] | Reaction temperature [° C.] | 3M1,3BDO conversion rate [%] | Selectivity Isoprene [%] | Isobutene [%] | Unsaturated alcohol [%] |
|---|---|---|---|---|---|---|---|---|---|
| Example 22 | 15 mol % CaO/YSZ | 700 | 4.0 | 0.43 | 350 | 100 | 53.1 | 3.5 | 36.5 |
| Example 15 | 15 mol % CaO/YSZ | 800 | 4.0 | 0.43 | 350 | 100 | 92.9 | 1.5 | 0.9 |
| Example 23 | 15 mol % CaO/YSZ | 900 | 4.0 | 0.43 | 350 | 100 | 90.0 | 4.0 | 1.4 |

TABLE I

| | Catalyst | Calcium content [mol-Ca/mol-Zr] | Calcination temperature [° C.] | Catalyst amount [g] | WHSV [h$^{-1}$] | Reaction temperature [° C.] | 1,3BDO conversion rate [%] | Selectivity 1,3-Butadiene [%] | MEK + MVK [%] | Unsaturated alcohol [%] |
|---|---|---|---|---|---|---|---|---|---|---|
| Example 24 | 15 mol % CaO/YSZ | 0.18 | 800 | 5.0 | 0.34 | 340 | 100 | 42.2 | 2.4 | 41.0 |
| Example 25 | 15 mol % CaO/YSZ | 0.18 | 800 | 5.0 | 0.34 | 360 | 100 | 76.5 | 4.2 | 7.5 |

TABLE I-continued

|  | Catalyst | Calcium content [mol-Ca/mol-Zr] | Calcination temperature [° C.] | Catalyst amount [g] | WHSV [h⁻¹] | Reaction temperature [° C.] | 1,3BDO conversion rate [%] | Selectivity | | |
|---|---|---|---|---|---|---|---|---|---|---|
|  |  |  |  |  |  |  |  | 1,3-Butadiene [%] | MEK + MVK [%] | Unsaturated alcohol [%] |
| Example 26 | 15 mol % CaO/YSZ | 0.18 | 800 | 5.0 | 0.34 | 380 | 100 | 86.7 | 1.5 | 0 |
| Comparative Example 6 | CeO₂ | — | 800 | 0.5 | 3.4 | 360 | 98.2 | 1.4 | 1.8 | 80.5 |
| Comparative Example 7 | CeO₂ | — | 800 | 5.0 | 0.34 | 360 | 100 | 11.4 | 33.0 | 26.7 |

From Table 3, it can be confirmed that, when the reaction is performed at a reaction temperature of 250° C. or higher, the conversion rate of 3M1,3BDO is 7.5% or more and the catalytic activity is exhibited. It is found that, as the reaction is performed at a higher temperature, the conversion rate is increased and the catalytic activity is increased. On the other hand, when the reaction is performed at a temperature of 400° C. or higher, there is a concern that coke is deposited on the catalyst to deteriorate the catalyst, which is disadvantageous.

From Table 4, in the case of a WHSV of 1.7 h⁻¹, the conversion rate close to 100% is obtained, but the unsaturated alcohol becomes a main product and there is room for causing the dehydration reaction to further proceed. On the other hand, when the WHSV is 1.1 h⁻¹ or less, isoprene that is a conjugated diene compound becomes a main product. As described above, it is found that, as the WHSV is decreased (the catalyst amount is increased), the selectivity of the conjugated diene compound is increased, and it is considered that, when the WHSV is 1.5 h⁻¹ or less, the selectivity of the conjugated diene compound is sufficient. When the WHSV is 0.1 h⁻¹ or less, the production rate per unit catalyst amount is decreased, which is not preferable.

From Table 5, in the case of a calcium content of 5 mol %, the selectivity of isoprene is 77.0% that is relatively high, and in the case of using YSZ of Comparative Example 2 not containing calcium as a catalyst, the selectivity of isoprene is 33.6% that is low. Therefore, when the calcium content is at least 1 mol % (0.01 mol) or more, isoprene becomes a main product, and when the calcium content is less than 1 mol %, the excessive decomposition suppressing effect by supporting calcium is not sufficiently exhibited so that isobutene of a decomposition product becomes a main product rather than isoprene.

On the other hand, from Table 5, when the calcium content is increased from 15 mol % to 20 mol %, the selectivity of isoprene is maintained to be high but is slightly decreased. Although the isoprene selectivity is considered to be high even when the calcium content is 20 mol % or more, when the calcium content exceeds 30 mol %, the active site of zirconium is excessively suppressed to decrease the catalytic activity, which is considered to be unfavorable.

From Table 6, it is found that, in the case of the catalyst calcined at 700° C. or higher, isoprene is mainly produced, and as the catalyst is calcined at a higher temperature, the isoprene selectivity is increased. In the case of the catalyst calcined at 700° C. or lower, there is a concern that the conversion rate is decreased. On the other hand, when the catalyst is calcined at a temperature of 1200° C. or higher, there is a concern that a surface area of the catalyst is decreased, and thereby the conversion rate is decreased.

From Table 7, it is found that, when 1,3BDO is used as a raw material, 1,3-butadiene is mainly produced, and this catalyst has not only the activity as a catalyst for producing isoprene but also the activity as a catalyst for producing 1,3-butadiene.

The invention claimed is:

1. A method for producing a conjugated diene, the method comprising:
    obtaining a fluid containing the conjugated diene that is isoprene by bringing fluid containing 3-methyl-1,3-butanediol into contact with a catalyst for producing the conjugated diene to remove two water molecules from one 3-methyl-1,3-butanediol molecule,
    wherein the catalyst comprises zirconium oxide and calcium oxide.

2. The method for producing a conjugated diene according to claim 1, wherein in said obtaining the fluid containing the conjugated diene, a mass flow rate (WHSV: Weight Hourly Space Velocity) of the 3-methyl-1,3-butanediol per unit time with respect to a weight of the catalyst for producing the conjugated diene is 1.5 h⁻¹ or less.

3. The method for producing the conjugated diene according to claim 1, wherein said obtaining the fluid containing the conjugated diene is performed at a reaction temperature within a range of 250° C. or higher and 400° C. or lower.

4. The method for producing the conjugated diene according to claim 1, further comprising:
    calcining the catalyst for producing the conjugated diene at a temperature within a range of 700° C. or higher and 1200° C. or lower before performing said obtaining the fluid containing the conjugated diene.

5. The method for producing the conjugated diene according to claim 1, wherein a content of calcium atom of the calcium oxide with respect to 1 mol of zirconium atom of the zirconium oxide is within a range of 0.01 mol or more and 0.3 mol or less in the catalyst.

6. The method for producing the conjugated diene according to claim 1, wherein the calcium oxide of the catalyst is supported on the zirconium oxide.

7. The method for producing the conjugated diene according to claim 1, wherein the zirconium oxide of the catalyst has a tetragonal form or a cubic form.

8. The method for producing the conjugated diene according to claim 1, wherein the zirconium oxide of the catalyst is yttria-stabilized zirconia (YSZ).

9. A method for producing a conjugated diene, the method comprising:
    obtaining a fluid containing the conjugated diene that is 1,3-butadiene by bringing fluid containing 1,3-butanediol into contact with a catalyst for producing the conjugated diene to remove two water molecules from one 1,3-butanediol molecule,
    wherein the catalyst comprises zirconium oxide and calcium oxide.

10. The method for producing a conjugated diene according to claim 9, wherein in said obtaining the fluid containing the conjugated diene, amass flow rate (WHSV) of the 1,3-butanediol per unit time with respect to a weight of the catalyst for producing the conjugated diene is $1.5 \text{ h}^{-1}$ or less.

11. The method for producing the conjugated diene according to claim 9, wherein said obtaining the fluid containing the conjugated diene is performed at a reaction temperature within a range of 250° C. or higher and 400° C. or lower.

12. The method for producing the conjugated diene according to claim 9, comprising calcining the catalyst for producing the conjugated diene at a temperature within a range of 700° C. or higher and 1200° C. or lower before performing said obtaining the fluid containing the conjugated diene.

13. The method for producing the conjugated diene according to claim 9, wherein a content of calcium atom of the calcium oxide with respect to 1 mol of zirconium atom of the zirconium oxide is within a range of 0.01 mol or more and 0.3 mol or less in the catalyst.

14. The method for producing the conjugated diene according to claim 9, wherein the calcium oxide of the catalyst is supported on the zirconium oxide.

15. The method for producing the conjugated diene according to claim 9, wherein the zirconium oxide of the catalyst has a tetragonal form or a cubic form.

16. The method for producing the conjugated diene according to claim 9, wherein the zirconium oxide of the catalyst is yttria-stabilized zirconia (YSZ).

\* \* \* \* \*